United States Patent
Mullaly

(10) Patent No.: US 9,517,114 B2
(45) Date of Patent: Dec. 13, 2016

(54) FIXED DETACHABLE DENTAL ATTACHMENT DEVICE, ASSEMBLY AND METHODS OF USING THE SAME

(75) Inventor: Scott Mullaly, San Marcos, CA (US)

(73) Assignee: ZEST IP HOLDINGS, LLC, Carlsbad, CA (US)

( * ) Notice: Subject to any disclaimer, the term of this patent is extended or adjusted under 35 U.S.C. 154(b) by 0 days.

(21) Appl. No.: 13/491,002

(22) Filed: Jun. 7, 2012

(65) Prior Publication Data

US 2012/0315599 A1 Dec. 13, 2012

Related U.S. Application Data

(60) Provisional application No. 61/494,544, filed on Jun. 8, 2011.

(51) Int. Cl.
*A61C 8/00* (2006.01)
*A61C 13/265* (2006.01)
*A61C 13/277* (2006.01)

(52) U.S. Cl.
CPC ......... *A61C 8/0048* (2013.01); *A61C 13/2656* (2013.01); *A61C 13/277* (2013.01)

(58) Field of Classification Search
CPC ..... A61C 13/2656; A61C 8/0048; A61C 8/00; A61C 8/005; A61C 8/006; A61C 8/0075; A61C 8/0059; A61C 8/0062; A61C 8/008; A61C 13/277; F16K 35/10; F16K 27/08; A61F 2/2814; A61F 2/30744; A61F 2002/30746; A61F 2002/30794; A61F 2002/30815; A61F 2002/464
USPC ............................... 433/173–176, 201.1, 172
See application file for complete search history.

(56) References Cited

U.S. PATENT DOCUMENTS

| 711,324 | A | | 10/1902 | Lacy |
| 866,340 | A | | 9/1907 | Roach |
| 3,514,858 | A | | 6/1970 | Silverman |
| 3,732,621 | A | * | 5/1973 | Bostrom ............... 433/174 |
| 3,787,975 | A | | 1/1974 | Zuest |
| 3,990,150 | A | | 11/1976 | Giovannini |
| 3,991,472 | A | | 11/1976 | Lukesch |

(Continued)

FOREIGN PATENT DOCUMENTS

| EP | 501940 A1 | 9/1992 |
| WO | 9518581 A1 | 7/1995 |

(Continued)

OTHER PUBLICATIONS

International Search Report and Written Opinion mailed on Oct. 1, 2012, in corresponding International Application No. PCT/US2012/041300, 13 pages.

(Continued)

*Primary Examiner* — Cris L Rodriguez
*Assistant Examiner* — Mirayda A Aponte
(74) *Attorney, Agent, or Firm* — Procopio, Cory, Hargreaves & Savitch LLP; Noel C. Gillespie

(57) ABSTRACT

A fixed, detachable dental attachment device comprising a cap for securing a dental appliance, a ring, and an abutment to attachment to a tooth root or implant. Also described herein are methods of securing a dental appliance in a subject's mouth by means of the dental attachment device. Further described herein is a dental attachment device for immediate load on a provisional denture and then incorporated into the final restoration.

21 Claims, 16 Drawing Sheets

(56) References Cited

U.S. PATENT DOCUMENTS

| | | | |
|---|---|---|---|
| 4,158,256 A | 6/1979 | Wiland et al. | |
| 4,290,755 A | 9/1981 | Scott | |
| 4,362,509 A | 12/1982 | Sulc | |
| 4,431,416 A | 2/1984 | Niznick et al. | |
| 4,475,891 A | 10/1984 | Hader | |
| 4,488,874 A | 12/1984 | Soifer | |
| 4,488,875 A | 12/1984 | Niznick | |
| 4,518,357 A | 5/1985 | Brinkmann et al. | |
| 4,540,367 A | 9/1985 | Sulc | |
| 4,547,156 A | 10/1985 | Hader | |
| 4,626,213 A | 12/1986 | Shiner et al. | |
| 4,645,453 A | 2/1987 | Niznick | |
| 4,657,510 A | 4/1987 | Gittleman | |
| 4,738,623 A | 4/1988 | Driskell | |
| 4,780,080 A | 10/1988 | Haris | |
| 4,793,808 A | 12/1988 | Kirsch | |
| 4,832,601 A | 5/1989 | Linden | |
| 4,854,872 A | 8/1989 | Detsch | |
| 4,907,969 A | 3/1990 | Ward | |
| 4,932,868 A | 6/1990 | Linkow | |
| 4,934,935 A | 6/1990 | Edwards | |
| 4,957,438 A | 9/1990 | Bax | |
| 4,988,297 A | 1/1991 | Lazzara | |
| 5,030,095 A | 7/1991 | Niznick | |
| 5,049,072 A | 9/1991 | Lueschen | |
| 5,071,350 A | 12/1991 | Niznick et al. | |
| 5,073,110 A | 12/1991 | Barbone | |
| 5,092,770 A | 3/1992 | Zakula | |
| 5,120,222 A | 6/1992 | Sulc | |
| 5,194,000 A | 3/1993 | Dury | |
| 5,195,891 A | 3/1993 | Sulc | |
| 5,211,561 A | 5/1993 | Graub | |
| 5,302,125 A | 4/1994 | Kownacki et al. | |
| 5,413,480 A | 5/1995 | Musikant et al. | |
| 5,417,570 A * | 5/1995 | Zuest | A61C 13/2656 433/172 |
| 5,480,304 A * | 1/1996 | Nardi | 433/172 |
| 5,520,540 A | 5/1996 | Nardi et al. | |
| 5,527,182 A | 6/1996 | Willoughby | |
| 5,556,280 A * | 9/1996 | Pelak | A61C 8/0048 433/172 |
| 5,564,924 A | 10/1996 | Kwan et al. | |
| 5,630,717 A | 5/1997 | Zuest | |
| 5,636,989 A | 6/1997 | Somborac et al. | |
| 5,639,239 A * | 6/1997 | Earle | A61C 5/08 433/218 |
| 5,678,997 A | 10/1997 | De Buck | |
| 5,839,898 A | 11/1998 | Fernandes et al. | |
| 5,954,505 A | 9/1999 | Ford | |
| 5,993,212 A | 11/1999 | Shiner | |
| 6,030,219 A * | 2/2000 | Zuest | A61C 8/0048 433/172 |
| 6,299,447 B1 | 10/2001 | Zuest et al. | |
| 6,302,693 B1 * | 10/2001 | Mena | A61C 8/0048 433/169 |
| 6,332,777 B1 | 12/2001 | Sutter | |
| 6,500,003 B2 | 12/2002 | Nichinonni | |
| 6,716,030 B1 | 4/2004 | Bulard et al. | |
| 6,843,653 B2 | 1/2005 | Carlton | |
| 6,981,871 B2 | 1/2006 | Mullaly et al. | |
| 7,704,076 B2 | 4/2010 | Mullaly et al. | |
| 8,128,403 B2 | 3/2012 | Karmon | |
| D666,298 S | 8/2012 | Sibhatu et al. | |
| 2005/0019730 A1 | 1/2005 | Gittleman | |
| 2006/0275735 A1 | 12/2006 | Bulard et al. | |
| 2008/0241790 A1 | 10/2008 | Gittleman | |
| 2009/0155745 A1 | 6/2009 | Laux | |
| 2009/0246734 A1 | 10/2009 | Bar Shalom | |
| 2010/0055645 A1 | 3/2010 | Mullaly et al. | |
| 2010/0129773 A1 * | 5/2010 | Chen | A61C 5/08 433/174 |
| 2010/0159420 A1 | 6/2010 | Mullaly et al. | |
| 2010/0232869 A1 * | 9/2010 | Ditzler et al. | 403/122 |
| 2010/0330536 A1 | 12/2010 | Mullaly | |
| 2012/0045737 A1 | 2/2012 | Ang | |
| 2012/0214128 A1 | 8/2012 | Collins et al. | |
| 2012/0288827 A1 | 11/2012 | McBride et al. | |
| 2014/0162211 A1 | 6/2014 | Mullaly et al. | |
| 2014/0162212 A1 | 6/2014 | Mullaly et al. | |

FOREIGN PATENT DOCUMENTS

| | | |
|---|---|---|
| WO | 2004004594 A1 | 1/2004 |
| WO | 2008040134 A1 | 4/2008 |
| WO | 2008079699 A2 | 7/2008 |
| WO | 2009156601 A2 | 12/2009 |
| WO | 2010025034 A1 | 3/2010 |

OTHER PUBLICATIONS

Langer, et al., Tooth-supported telescopic prostheses in compromised definitions: A clinical report, The Journal of Prosthetic Dentistry, 84(2); 129-132(2000.

ISR and Written Opinion mailed Oct. 1, 2012, in corresponding International Application No. PCT/US2012/041300, 11 pages.

International Search Report and Written Opinion for PCT/US2013073145, dated Mar. 19, 2014 (8 pages).

International Search Report and Written Opinion for PCT/US2012041300, dated Sep. 20, 2012.

Communication Pursuant to Article 94(3) EPC, dated Mar. 19, 2014 for European Patent Application No. 03763001.9-1659—5 pages.

* cited by examiner

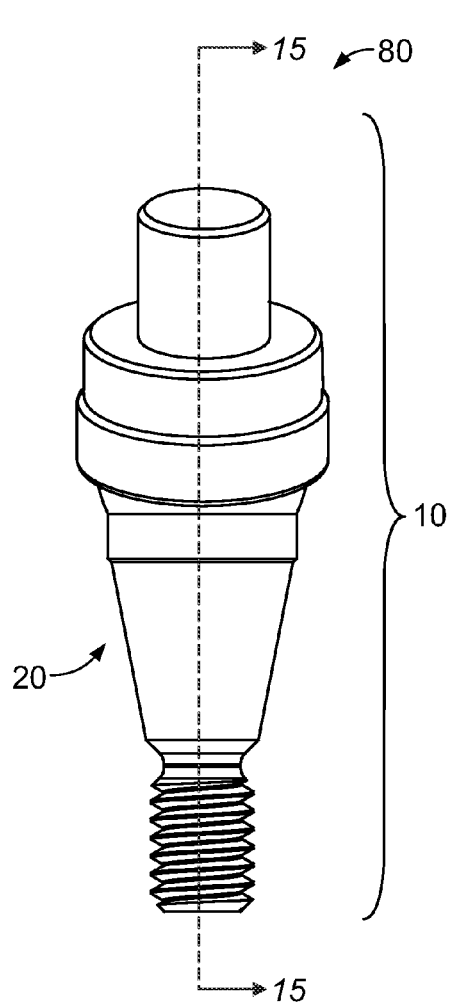
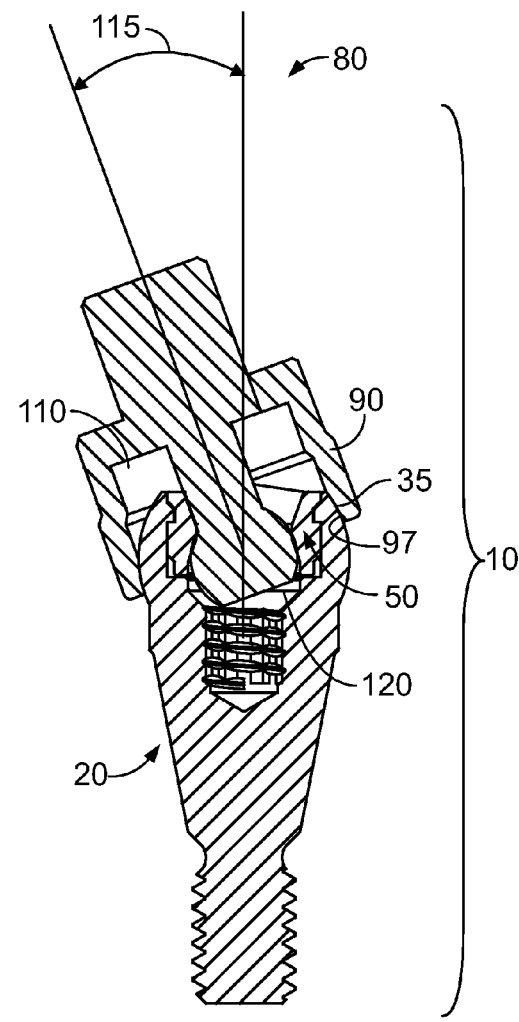
FIG. 14
FIG. 15

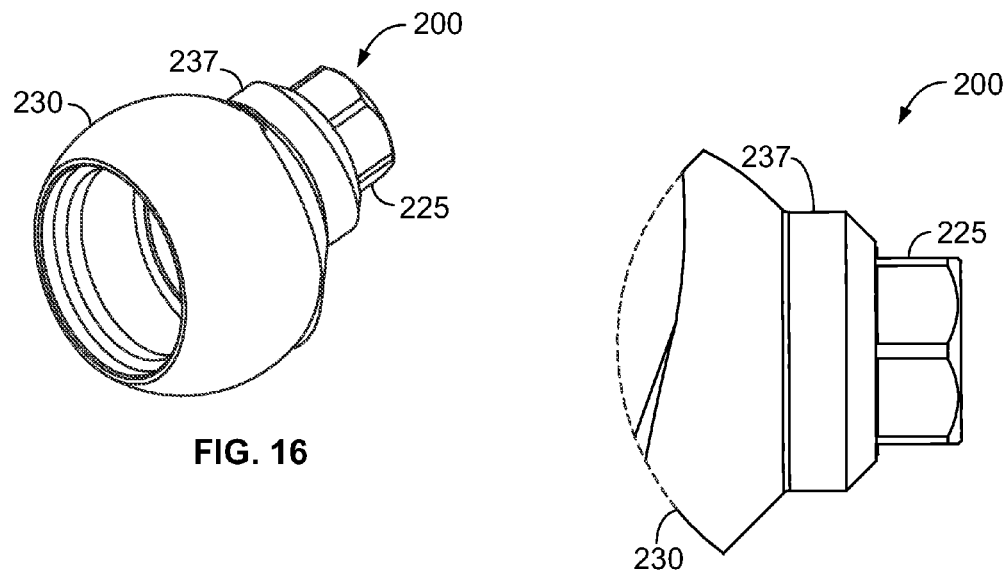
FIG. 16
FIG. 17
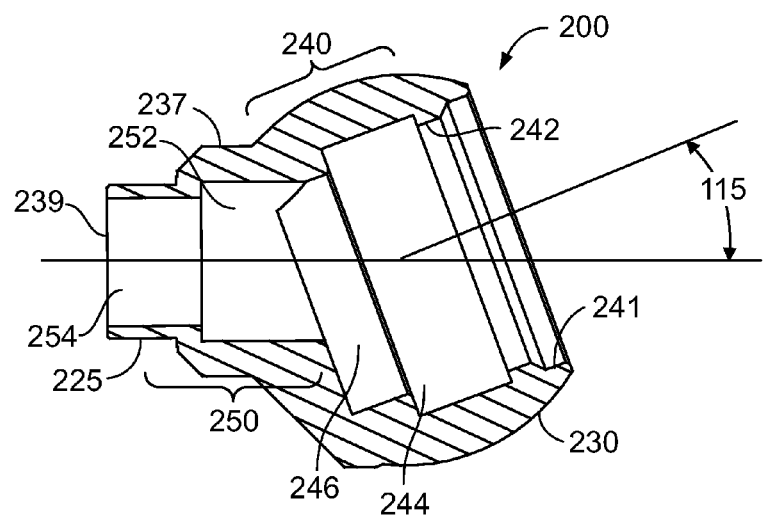
FIG. 18

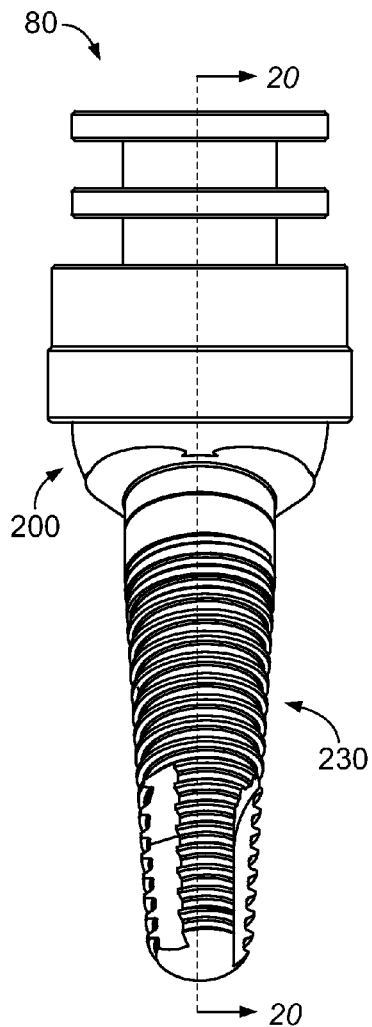
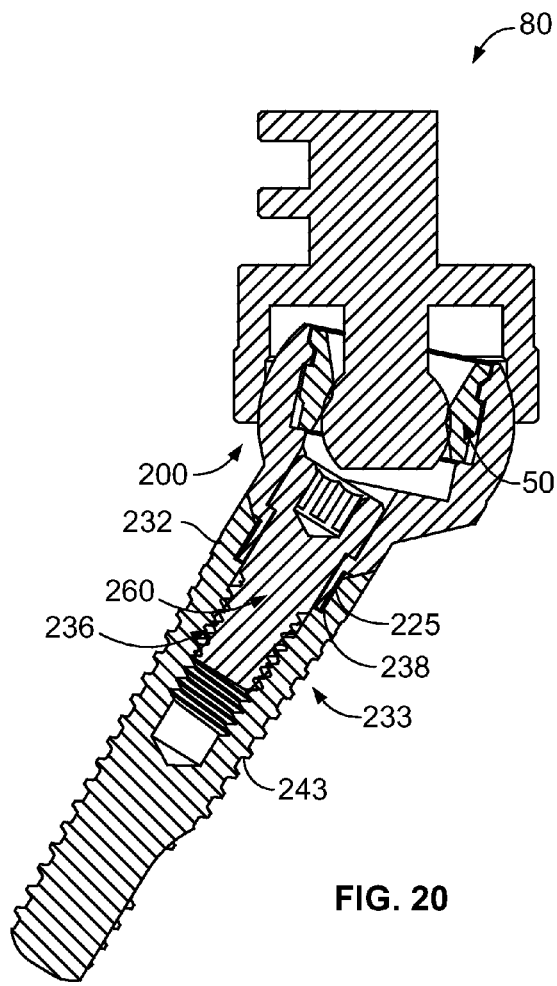
FIG. 19
FIG. 20

FIXED DETACHABLE DENTAL ATTACHMENT DEVICE, ASSEMBLY AND METHODS OF USING THE SAME

RELATED APPLICATIONS

This application claims priority to U.S. Provisional Patent Application No. 61/494,544, filed Jun. 8, 2011, which is incorporated by reference herein in its entirety to the extent permitted by law.

FIELD

The present invention relates to fixed detachable dental attachment devices and assemblies, and methods of using the same for securing a dental appliance.

BACKGROUND

A denture is a prosthetic device constructed to replace some or all of the missing natural teeth in a patient's mouth. There are two types of dentures: a partial denture and a complete denture. The partial denture replaces a few missing teeth, while the complete denture substitutes the entire maxillary and/or mandibular arch. Dentures can be secured to dental implants or non-vital tooth roots in the mouth of a patient using either a removable or fixed attachment system. In general, a removable denture is designed and fabricated to be attached to dental implants and removed by the patient, whereas a fixed denture is attached to dental implants using cement or screws and can only be removed by a dental care provider.

Both the removable and fixed implant supported dentures have their advantages and disadvantages. Common advantages for both the removable and fixed dentures include: proper chewing, protection of the gums, and improvement in speech and aesthetics. Removable dentures are less costly and allow for easier cleaning to promote oral hygiene on a daily basis and fewer long-term treatment complications. However, they lack the feel of natural teeth and require more maintenance, e.g., replacement and/or adjustment of attachments and attachment components. In contrast, fixed dentures feel more like natural teeth with less food entrapment and less maintenance. Fixed dentures also distribute occlusal loading onto the implant and onto the jaw bone, which can be beneficial to maintenance of the bone ridge height and thickness, bone quality, and oral and facial aesthetics. Nevertheless, fixed dentures are more expensive and more difficult in terms of long-term treatment complications.

Conventional fixed dental implant attachments systems generally have higher treatment costs and involve more complicated procedures. The cost of components and laboratory fees contribute, in part, to high treatment costs that restrict access of such conventional fixed attachment systems. At the same time, complicated techniques, such as accommodating implant angulations, verification try-ins, and difficulty with administering cement and/or screws, increase complexity that requires highly skilled dental care providers, which further adds to the high cost of treatment. Likewise, maintenance of conventional fixed attachment system require time consuming procedure and high cost as the system and/or system components must be removed and replaced at recall appointments.

Accordingly, there is a need in the art for a simple, low cost, screwless, cementless, fixed dental implant attachment system that is detachable by the dental care provider, but at the same time provides the benefits of a fixed dental attachment system. Disclosed herein is a unique, simple, lower cost, fixed but clinically detachable device for those patients who want the advantages of a "fixed" implant supported denture but cannot afford the current higher end options, and an entry point allowing less experienced dentists to perform fixed restorations due to an easier restorative procedure. Further described herein is a dental implant attachment device that can provide for immediate load (function), through components that can be easily used with the provisional denture and then incorporated into the final restoration.

SUMMARY OF THE INVENTION

Described herein is a detachable fixed dental attachment device, a dental attachment assembly, and methods of securing a dental appliance in a subject's mouth using the same. In one embodiment, a dental attachment device comprises a cap for securing a dental appliance, a retainer ring, and an abutment. The cap may be integral with a dental appliance, such as a full denture, overdenture, or partial denture. Depending on the extent of the dental appliance, one or more abutments may be present in the subject's mouth with corresponding caps being integral with the dental appliance.

Though the fixed detachable abutment and denture cap have internal features generally consistent with the geometry of O-Ring or O-Ball attachment systems, it is substantially differentiated in two principal ways. First, the fixed detachable abutment is designed to rigidly connect the prosthesis (i.e. denture) to dental implants and remain in place with only periodic removal (i.e. once or twice a year for hygiene maintenance) by a clinician with use of a tool specifically designed for that purpose. Conversely, O-Ring or O-Ball attachment systems provide substantially less retentive force and are designed to be used with a removable prosthesis, allowing the patient to easily take out and replace their denture on a routine (i.e. daily) basis.

Second, the fixed detachable abutment system attaches the prosthesis directly to a dental implant thereby transferring all mastication loads to a series of implants that are integrated in the patient's jaw. The O-Ring or O-Ball systems are solely intended to provide resilient retention of the denture in the mouth with the prosthesis seating directly on the soft tissue, or gingiva, which absorbs substantially all intra-oral forces such as those from mastication. This is an important distinction as tissue borne dentures are typically more uncomfortable for a patient because the prosthesis can compress, abrade and pinch the gums during chewing function.

Other embodiments, objects, features, and advantages will be set forth in the detailed description of the embodiments that follow and, in part, will be apparent from the description or may be learned by practice of the claimed invention. These objects and advantages will be realized and attained by the devices, assemblies, and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 14 is a side view of the assembled dental attachment device of FIG. 1 with a divergence between the cap and abutment.

FIG. 15 is a cross-sectional view of FIG. 14.

FIG. 16 is a perspective view of 20° pre-angled abutment.

FIG. 17 is a side view of FIG. 16.

FIG. 18 is a cross-sectional view of FIG. 17.

FIG. 19 is a side view of the assembled dental attachment device with a 20° pre-angled abutment of FIG. 16

FIG. 20 is a cross-sectional view of FIG. 19.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated and/or described, and should not be construed to limit the scope or breadth of the present invention. The headings used throughout this disclosure are provided for convenience only and are not to be construed to limit the claims in any way. Embodiments illustrated under any heading may be combined with embodiments illustrated under any other heading.

In certain embodiments, the present invention relates to a detachable dental attachment device, comprising a cap, a ring, and an abutment. The cap secures a dental appliance and has an open end and an inner cavity that forms an annular wall surrounding a retention head. The abutment comprises an upper portion having a convex outer surface. The convex outer surface has an open end and an internal socket for receiving the ring and engaging the retention head. The dental appliance may be secured in a subject's mouth by attaching the abutment into an existing non-vital tooth root or implant, aligning the cap over the abutment, and engaging the retention head through the ring and into the socket of the abutment thereby securing the cap (and dental appliance) onto the abutment.

The fixed detachable abutment and denture cap described herein have internal features generally consistent with the O-Ring or O-Ball attachment systems, however, it is substantially differentiated in two principal ways. First, the fixed detachable abutment is designed to rigidly connect the prosthesis to dental implants and remain in place with only periodic removal by a clinician with use of a tool specifically designed for that purpose. Conversely, O-Ring or O-Ball attachment systems provide substantially less retentive force and are designed to be used with a removable prosthesis, allowing the patient to easily take out and replace their denture on a daily basis. Second, the fixed detachable abutment system attaches the prosthesis directly to a dental implant thereby transferring all mastication loads to a series of implants that are integrated in the patient's jaw. In contrast, the O-Ring or O-Ball systems are solely intended to provide resilient retention of the denture in the mouth with the prosthesis seating directly on the soft tissue, or gingiva, which absorbs substantially all intra-oral forces such as those from mastication. This is an important distinction as tissue borne dentures are typically more uncomfortable for a patient because the prosthesis can compress, abrade and pinch the gums during chewing function.

The present invention further contemplates a kit comprising one or more detachable dental attachment devices and one or more tools designed for periodic removal.

Figure 1:
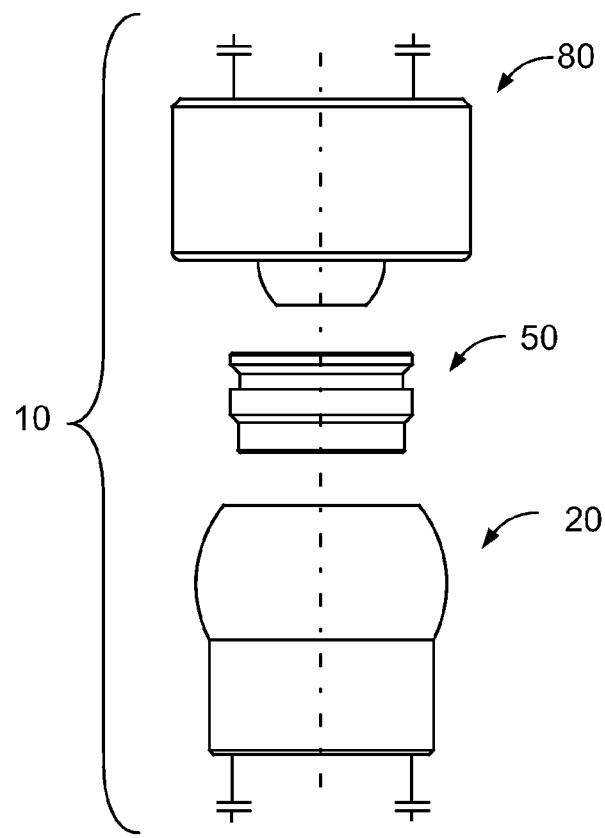
FIG. 1 is an exploded view of the dental attachment device.

FIG. 1 illustrates one embodiment of the dental attachment device for securing a dental appliance in the mouth of a subject. FIG. 1 is an exploded view of the dental attachment device 10 comprising: a cap 80 for securing in the dental appliance, an abutment 20 for attachment to a non-vital tooth root, implant or the like, and a retainer ring 50. The cap 80 engages with the abutment 20 and ring 50 as indicated by the center line of FIG. 1 to secure a dental appliance in the mouth of a subject. The abutment 20 may be adapted to be compatible with commercially available implants, such as the Astra implant (Astra Tech Inc., Waltham, Mass.), Brånemark implant (Nobel Biocare, Zurich, Switzerland), and the Straumann implants (Straumann USA LLC, Andover, Mass.), or configured as a tooth root abutment, mini-implant, or in a configuration that can be adapted to an intermediary abutment, which would be secured to a dental implant. Likewise, the cap 80 may be designed to integrate in a dental appliance by means of, for example but not limited to, a post, a screw, or an adhesive, such as acrylic, bisacrylic, or other dental cements. Dental appliances include, but are not limited to, full dentures, overdentures, and partial dentures. Thus, depending on the extent of the dental appliance, one or more dental attachment devices 10 may be used to fix the dental appliance in the patient's mouth.

Figure 2:
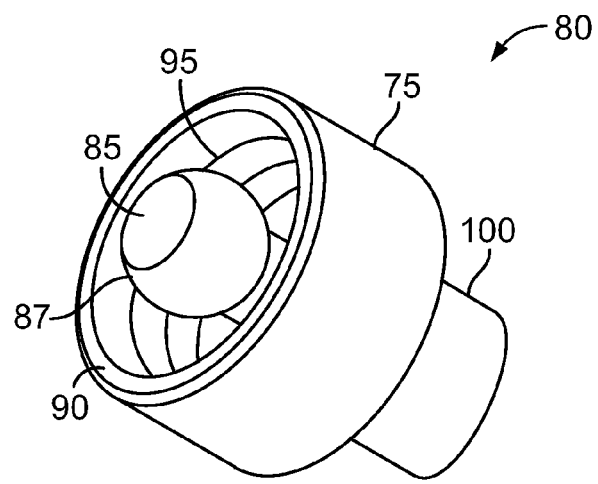
FIG. 2 is a perspective view of a cap.
Figure 3:
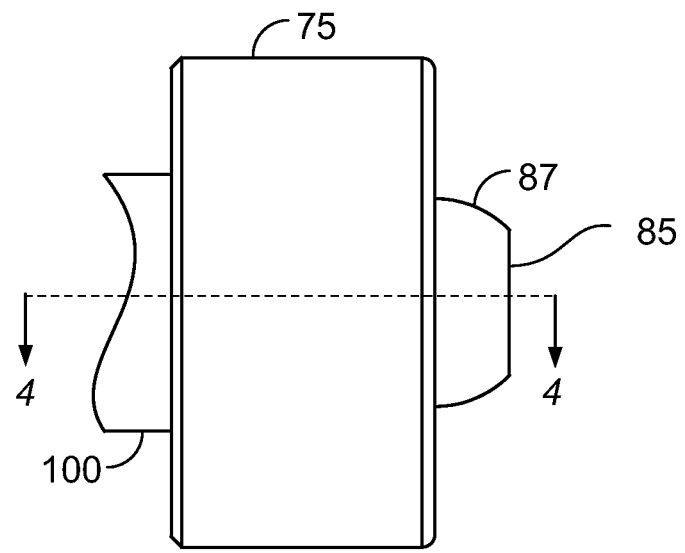
FIG. 3 is a side view of FIG. 2.
Figure 4:
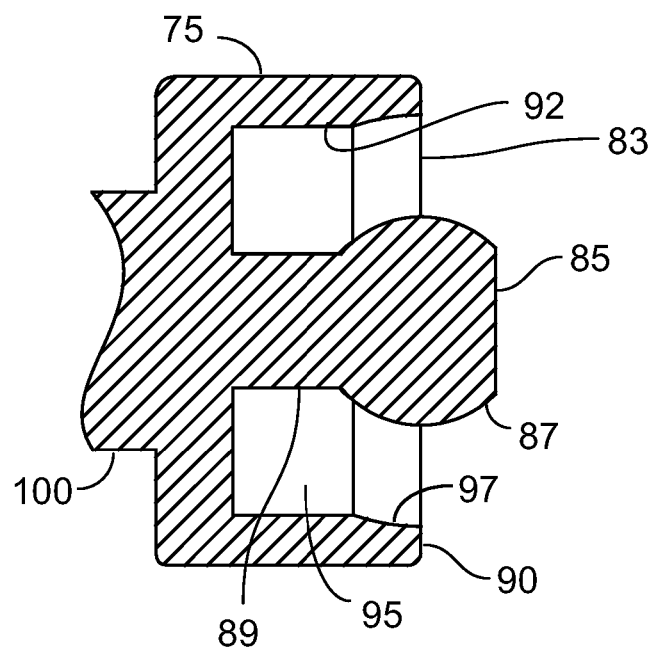
FIG. 4 is a cross-sectional view of FIG. 3.
Figure 5:
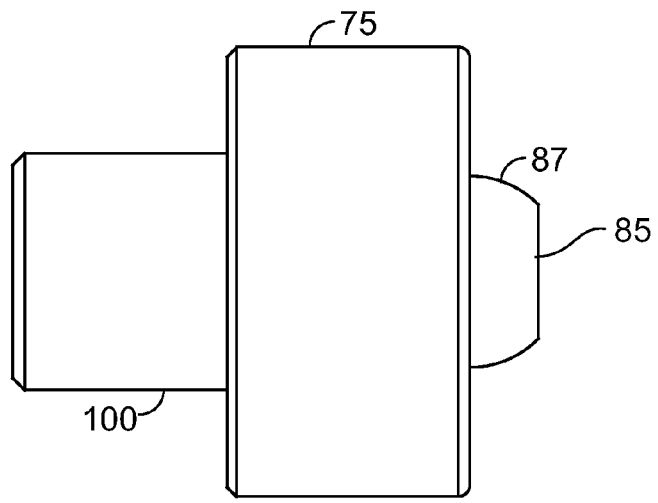
FIG. 5 is a side view of a cap having a short post attachment.
Figure 6:
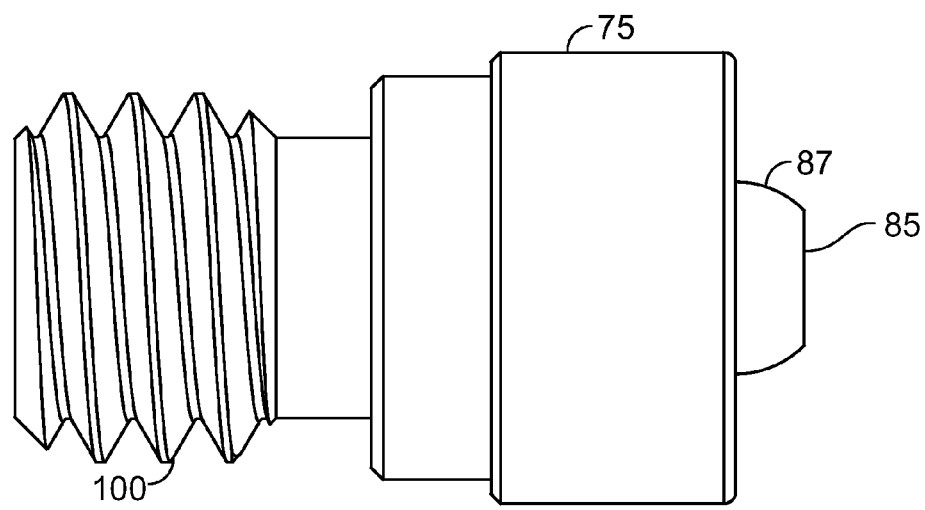
FIG. 6 is a side view of a cap having a screw attachment.
Figure 7:
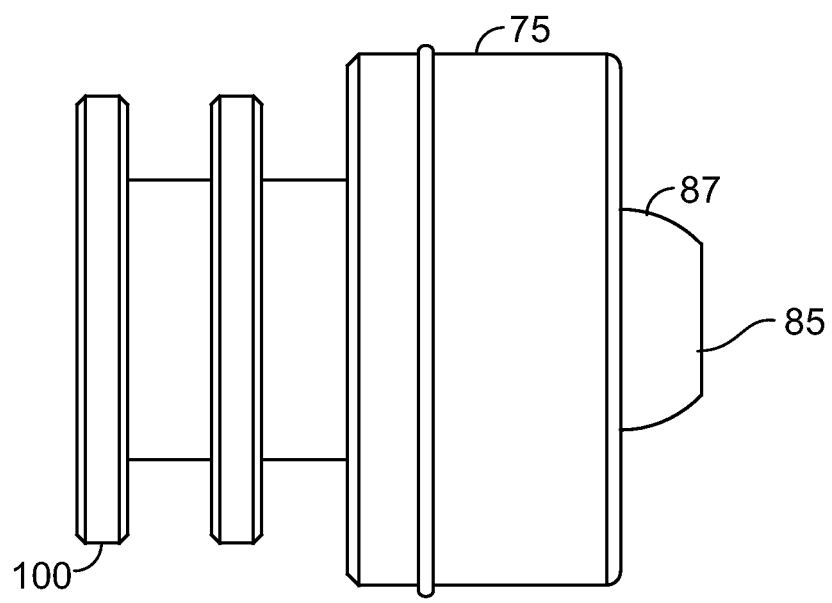
FIG. 7 is a side view of a cap having an adhesive attachment.

FIGS. 2 to 4 illustrate one embodiment of the cap 80. The cap 80 Comprises a first attachment portion 100 and a body portion 75, the body portion 75 having an open end 83 and an inner cavity 95 forming an annular wall 90. The body portion 75 may be any shape suitable for securing the cap 80 in a dental appliance. By way of example, FIGS. 2 to 4 represent the outer shape as generally cup-shaped or cylindrical. The inner cavity 95 has an inner annular surface 92 with a distal end portion having a concave lip 97. The concave lip 97 is designed to correspond with the outer convex surface 35 of the abutment 20. The annular wall 90 surrounds a retention head 85 comprising a head portion 87 and a shaft 89. The head portion 87 is substantially spherical or ball-shaped. In alternative embodiments, the head portion 87 may be substantially polygonal or spheroid. The head portion 87 can project above the lip of the annular wall 90. In an alternative embodiment, the head portion 87 can be level or below the lip of the annular wall 90. The first attachment portion 100 is provided to secure in the dental appliance by structures or techniques well known and understood by those skilled in the art, including but not limited to, a short post (FIG. 5), a screw (FIG. 6), or an adhesive (FIG. 7). Such methods and techniques will not be repeated herein, and the figures are provided as exemplary only and not meant to limit the techniques of attaching the cap to a dental appliance.

In one embodiment, the cap 80 can be integral with the dental appliance and made of titanium, titanium alloys, cobalt-chromium-molybdenum alloys, stainless steel with a titanium nitride coating, zirconium, tantalum, gold, platinum, palladium, hafnium and tungsten, as well as other materials known to those of skill in the art. Both the first attachment portion 100 and body portion 75 may be recessed in the dental appliance. In another embodiment, the body portion 75 may be partially recessed in the dental appliance. In still another embodiment, only the first attachment portion 100 may be recessed in the dental appliance.

In one embodiment of the cap 20, the head portion 87 has a diameter in the range of about 0.05 in to about 0.15 in. Illustratively, the diameter of the head portion 87 is about 0.05 in, about 0.06 in, about 0.07 in, about 0.08 in, about 0.09 in, about 0.10 in, about 0.11 in, about 0.12 in, about 0.13 in, about 0.14 in, and about 0.15 in.

Figure 8:
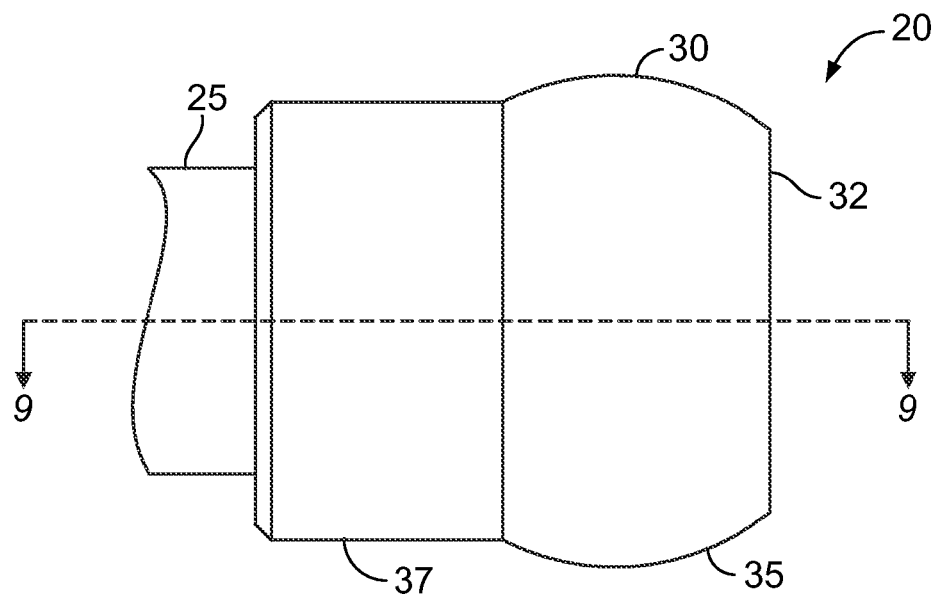
FIG. 8 is a side view of an abutment.
Figure 9:
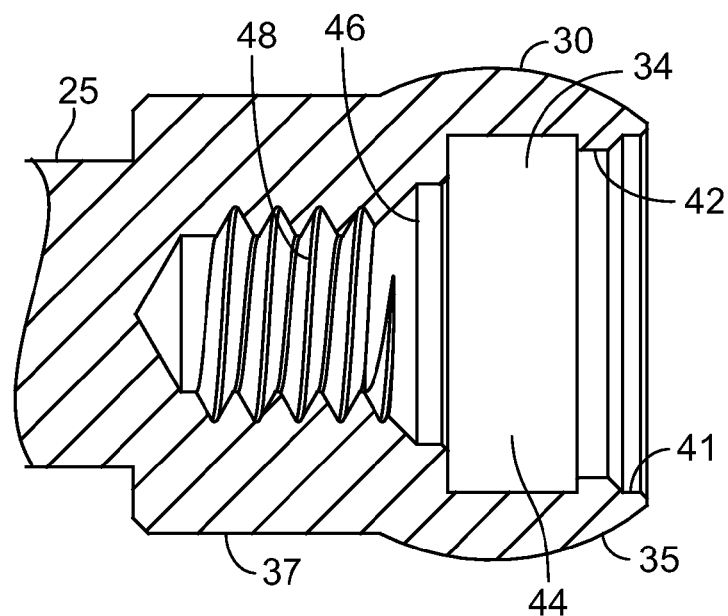
FIG. 9 is a cross-sectional view of FIG. 8.

FIGS. 8 and 9 illustrate one embodiment of the abutment 20. The abutment comprises a upper portion 30 having an open end 32 and a socket 34 for receiving the ring 50 and the retention head 85 of the cap 80, a cuff portion 37, and a second attachment portion 25 for attachment to a non-vital tooth root or implant. The upper portion 30 has a convex outer surface 35 extending from the open end 32 to the cuff portion 37. The cuff portion 37 may be of different heights to accommodate patients with different tissue heights. The socket 34 extends from the open end 32 through part or all of the length of the upper portion 30 and/or cuff portion 37, and is designed to accommodate the ring 50 and the retention head 85 of the cap. The socket 34 has an annular lip 41, an annular ring 42, a cylindrical cavity 44, and a hemispherical or bowl-shaped portion 46. The cavity 44 receives the ring 50 by snap-engagement over the annular ring 42 of the abutment 20, which fits into the corresponding annular groove 60 of the ring 50. The head portion 87 of the retention head 85 snap-fits through the ring 50 and is positioned in the hemispherical portion 46, securing the cap onto the abutment. A tool-receiving bore 48 extends inwardly from the bottom of the socket 34 and can be threaded or polygonal, for example, hexagonal with flat faces, for engagement by a suitable tool for attaching the abutment 20 to a non-vital tooth root or implant. The second attachment portion 25 can be adapted to be compatible with commercially available implants, or configured as a tooth root abutment, mini-implant, or an intermediary abutment as discussed below.

The abutment 20 described herein can be made of suitably strong material such as titanium, titanium alloys, cobalt-chromium-molybdenum alloys, stainless steel with a titanium nitride coating, zirconium, tantalum, gold, platinum, palladium, hafnium and tungsten, as well as other materials known to those of skill in the art. The abutment 20 can be made in a range of different sizes to fit a number of different implants, tooth roots, or intermediary abutment. The length of the abutment 20 is in the range of about 1 mm to about 10 mm. In further embodiments, the length can be about 1 mm, about 2 mm, about 3 mm, about 4 mm, about 5 mm, about 6 mm, about 7 mm, about 8 mm, about 9 mm, and about 10 mm.

Figure 10:
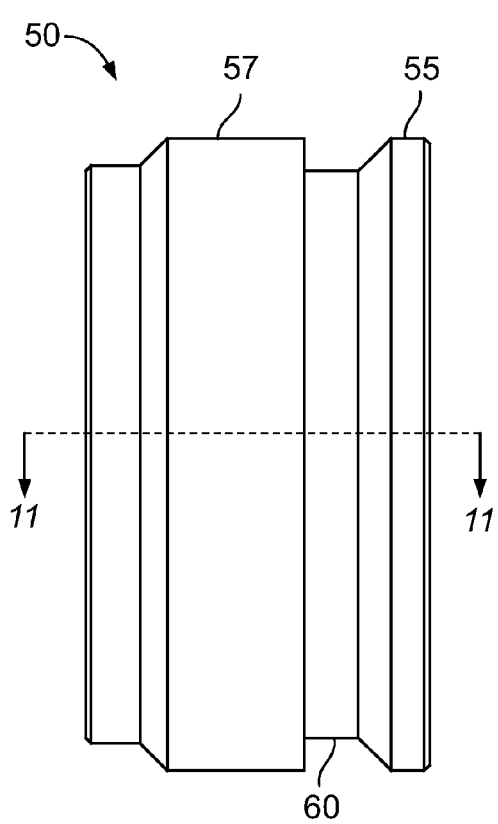
FIG. 10 is a side view of a ring.
Figure 11:
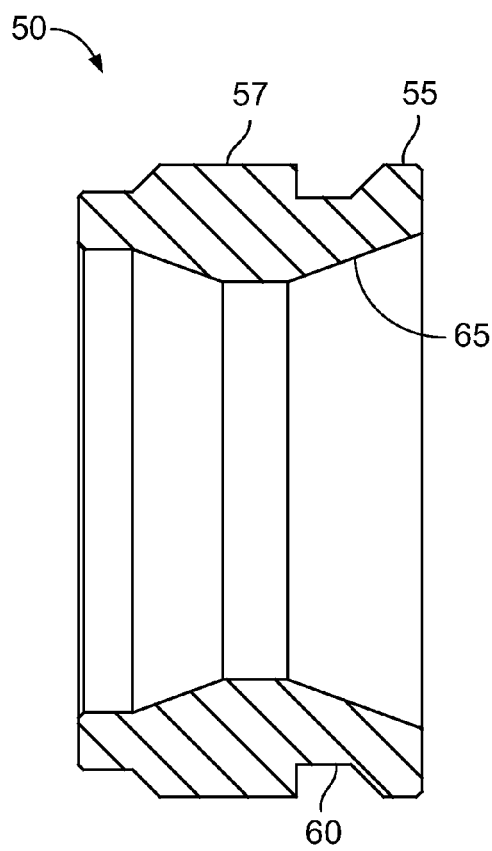
FIG. 11 is a cross-sectional view of FIG. 10.

The ring 50, shown in FIGS. 10 and 11, is adapted for engagement in the socket 34 of the abutment 20 for retention of cap 80, which is integral with the dental appliance. Referring to FIG. 10, the ring 50 has two annular flanges 55 and 57 separated by an annular seat or groove 60 to receive the corresponding annular ring 42 in the socket 34 of the abutment 80. The inner surface 65 of the ring 50, as shown in FIG. 11, is inwardly tapered from both the top and bottom, forming an hour-glass shape. The ring 50 can be made of suitably durable and flexible material such as nylon, PEEK, delrin, and other polymers known in the art, and metals such as titanium, stainless steel, etc., as well as other materials known to those of skill in the art.

Figure 12:
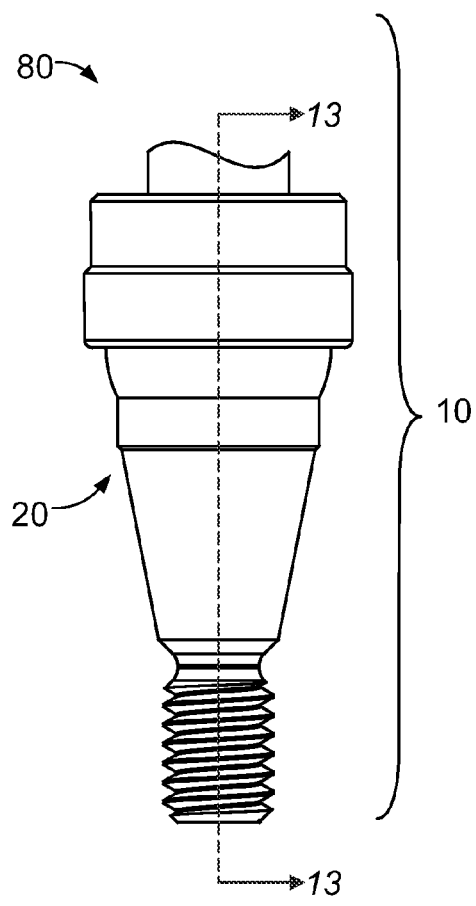
FIG. 12 is a side view of the assembled dental attachment device of FIG. 1.
Figure 13:
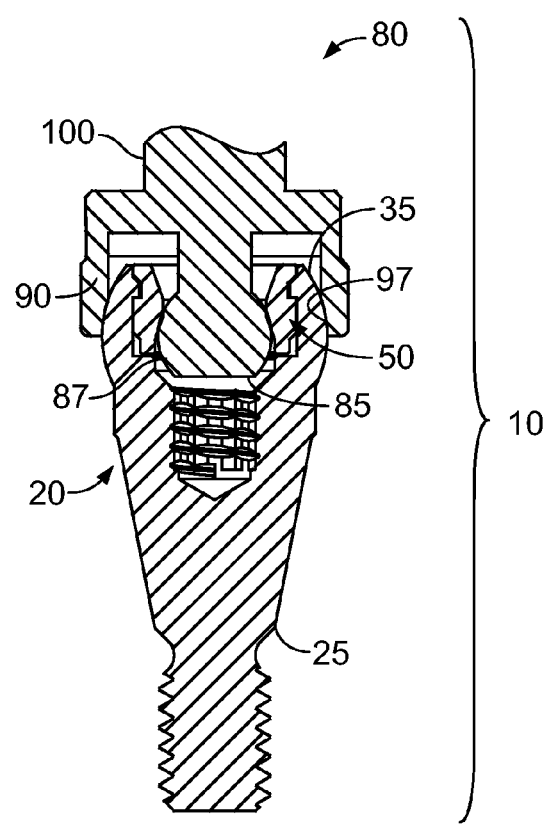
FIG. 13 is a cross-sectional view of FIG. 12.

FIGS. 12 and 13 illustrate one embodiment of the assembled dental attachment device for securing a dental appliance in the mouth of a patient. To assemble the dental attachment device, the ring 50 is snap fit over the annular ring 42 into the cylindrical cavity 44. The cap 80 (which can be integral with a dental appliance) is positioned over the abutment, and the retention head 85 is engaged into the socket 34 and snap fit through the ring 50. The head portion 87, or a portion thereof, is received into the hemispherical or bowl-shaped portion 46. The snap-fit engagement of the head portion 87 of the retention head 85 and ring 50 secures the cap onto the abutment. At the same time, the annular wall 90, in particular the concave lip 97, is engaged over the convex outer surface 35 of the abutment 20. The frictional forces, as well as the angle of convergence, between the two corresponding surfaces 97 and 35 also secures the cap to the abutment, while at the same time allow for a range of divergence between the cap 80 relative to the abutment 20. The tightened fit between the cap 80 and abutment 20 helps to seal the device from oral fluids in an effort to prevent microbial contamination and plaque traps.

Referring to FIGS. 14 and 15, when the dental attachment device 10 is assembled, there is a gap 110 between the cap 80 and the abutment 20 and a gap 120 between the ball-type head portion 87 and the hemispherical or bowl-shaped portion 44, which allows the cap 20 to diverge or pivot or swivel relative to the abutment 20. The range of divergence between the cap 80 and abutment 20 is 0° to about 20°. Illustratively, the cap diverges relative to the abutment at an angle of 0°, about 1°, about 2°, about 3°, about 4°, about 5°, about 6°, about 7°, about 8°, about 9°, about 10°, about 11°, about 12°, about 13°, about 14°, about 15°, about 16°, about 17°, about 18°, about 19°, and about 20°. The divergence of the cap 80 relative to the abutment 20 is shown as reference numerical 115. However, even at the range of divergence, the annular wall 90 (and concave lip 97) maintains contact with the outer surface 35 of the abutment 20 to ensure frictional contact and help to create a seal between the cap 80 and abutment 20.

FIGS. 16 to 18 illustrate one embodiment of a pre-angled abutment 200. The pre-angled abutment 200 is similar to that of the previous embodiment described in FIGS. 8 to 9. Referring to FIGS. 16 to 18, the pre-angled abutment 200 comprises an upper portion 230, a cuff portion 237, a second attachment portion 225, and a through bore 239. The through bore 239 comprises a first portion 240 and a second portion 250. The first portion 240 is similar to socket 34 of FIG. 9, having an annular lip 241, annular ring 242, a cylindrical cavity 244, and a lower portion 246. The cavity 244 receives the ring 50 by snap-engagement over the annular ring 42 of abutment 20, which fits into the corresponding annular groove 60 of the ring 50. The head portion 87 of the retention head 85 snap-fits through the ring 50 and is positioned in the lower portion 246. The second portion 250 comprises a first cylindrical portion 252, that accepts a retaining screw to fasten a pre-angled abutment to an implant, and a second cylindrical portion 254, the second cylindrical portion 254 having a smaller diameter than the first cylindrical portion 252.

In one embodiment, the upper portion 230 is at an angled of 20° from a central axis of the cuff 237 and attachment 225 portions as shown in FIG. 18. The pre-angled abutment is exemplary and not limiting as the pre-angled abutment can be at an angle of, about 10°, about 15, about 20°, and about 25°. In additional embodiments, the pre-angle abutment can be at an angle between about 5° to about 45°, about 10° to about 40°, about 15° to about 35°, and about 20° to about 30°. By way of example, the 20° pre-angled abutment, together with the range of divergence, allows a divergence up to about 40° of the cap 80 relative to the central axis of the cuff 237 and attachment 225 portions of the abutment 20. Illustratively, the range of divergence of the cap 20 is about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, and about 400° relative to the 20° pre-angled abutment 200.

Referring to FIGS. 19 and 20, the pre-angled abutment 200 can be secured in an implant 233 by means of the second attachment portion 225, which is secured in an implant using a retaining screw 260. The implant 233 comprises a first end cuff portion 232 having an open end comprising a cavity 238 for receiving the second attachment portion 225 of the pre-angled abutment 200 and a threaded bore 236, and a second end thread shaft 243. The cavity 238 is designed in size and shape to mate with the second attachment portion 225 of abutment 200. For assembly, the second attachment portion 225 of the pre-angled abutment 200 is fitted into the cavity 238 of the implant 233. The retaining screw 260 is set through the through bore 239 and screwed into the threaded bore 236, thereby securing the pre-angled abutment 200 to the implant 230.

Figure 21:
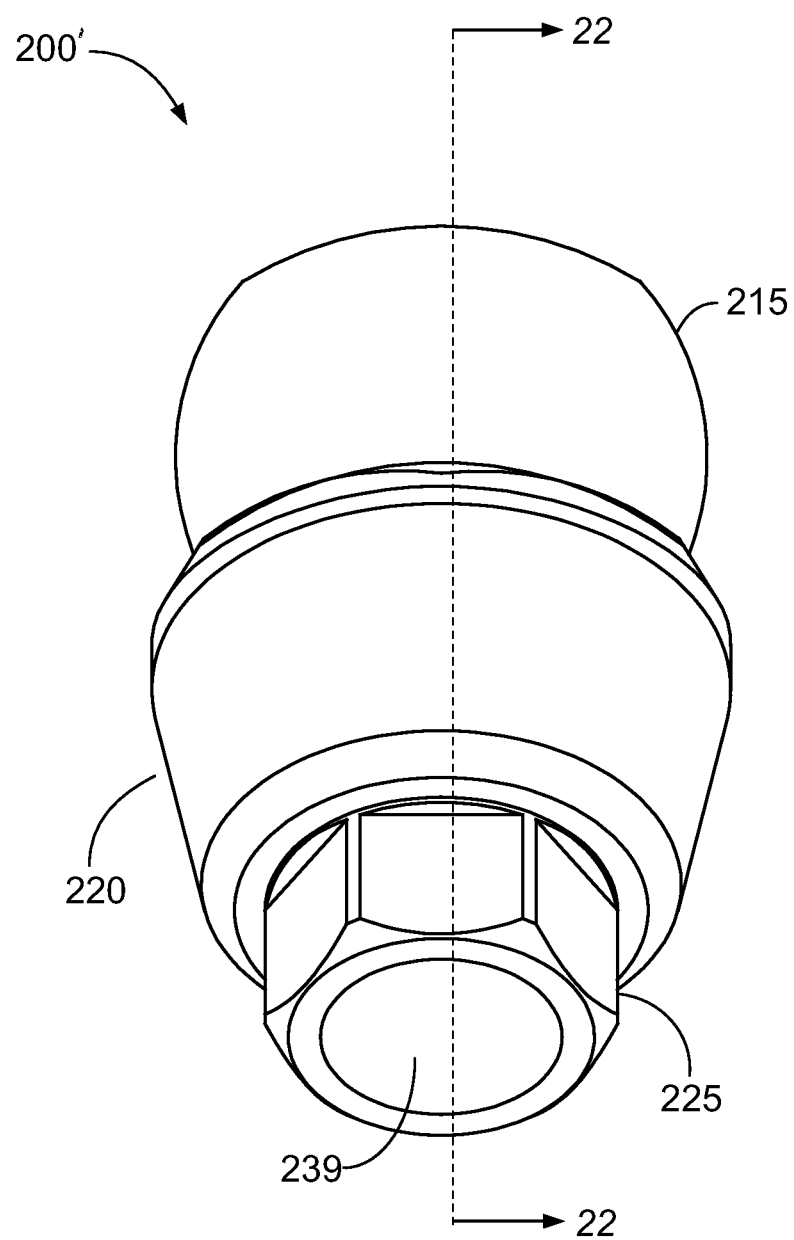
FIG. 21 is an alternative embodiment of a 20° pre-angled abutment.
Figure 22:
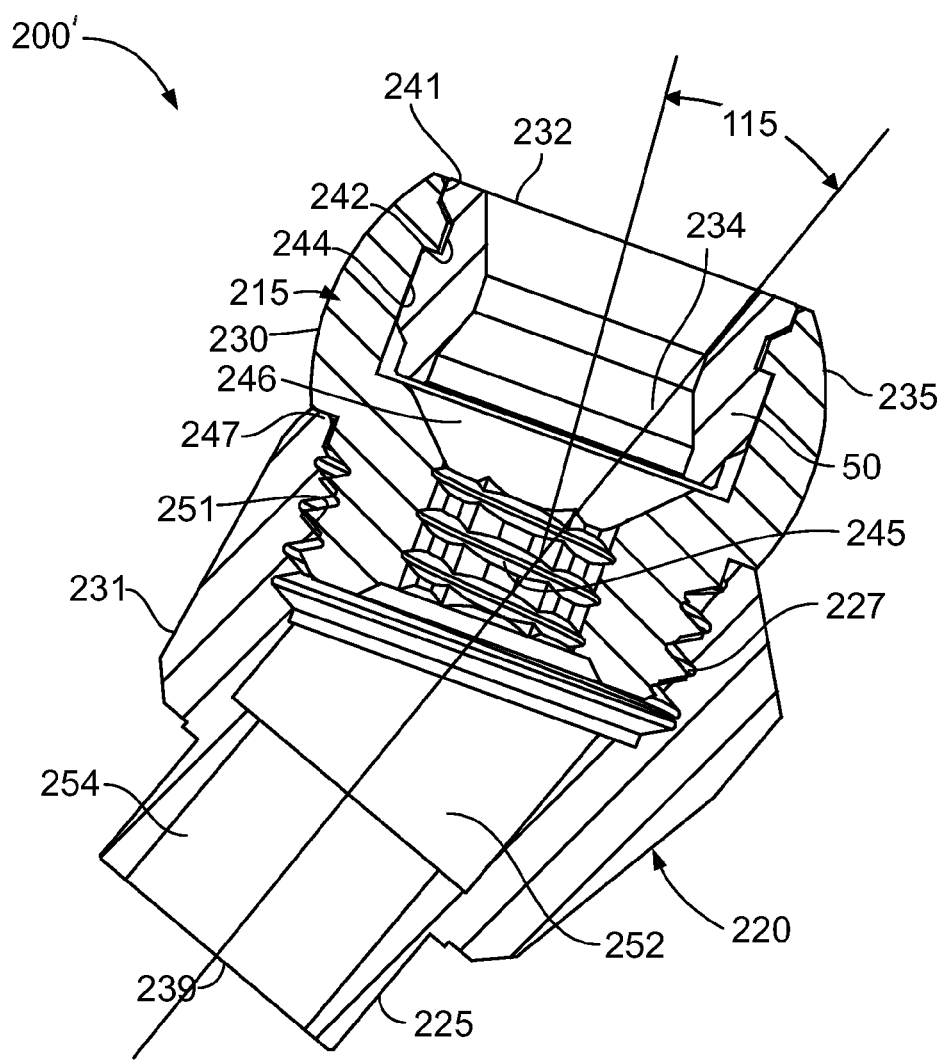
FIG. 22 is a cross-sectional view of FIG. 21.

An alternative embodiment of a two-piece pre-angled abutment 200' is illustrated in FIGS. 21 and 22. The pre-angled abutment 200' is similar to that of the previous embodiment described in FIGS. 16 to 18, and like reference numbers will be used for like parts. The pre-angled abutment 200' comprises a first component 215 having an upper portion 230 and a threaded shaft 227, and a second component 220 having a body portion 231, a second attachment portion 225, and through bore 239. The upper portion 230 has an open end 232 and a socket 234 for receiving the ring 50 and the retention head 85 of the cap 80, and a convex outer surface 235 extending from an open end 232 to the threaded shaft 227. The socket 234 has an annular lip 241, annular ring 242, a cylindrical cavity 244, and a lower portion 246. A tool-receiving bore 245 extends inwardly from the bottom of the socket 234. The body portion 231 has a open end 247 and a cavity having a thread portion 251, a first cylindrical portion 252, and a second cylindrical portion 254 having a smaller diameter than the first cylindrical portion 252.

The thread portion 251 is at a predetermined angled 115 from a central axis of the first and second cylindrical portions 252 and 254, respectively, and in turn, when assembled, the first component will be at the same predetermine angle. For example, the pre-angled abutment can be at an angle of, about 10°, about 15, about 20°, and about 25°. In additional embodiments, the pre-angle abutment can be at an angle between about 5° to about 45°, about 10° to about 40°, about 15° to about 35°, and about 20° to about 30°. By way of example, the 20° pre-angled abutment, together with the range of divergence, allows a divergence up to about 40° of the cap 80 relative to the first and second cylindrical portions 252 and 254, respectively, of the abutment 200'. Illustratively, the range of divergence of the cap 20 is about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, and about 40° relative to the 20° pre-angled abutment 200'.

Figure 23:
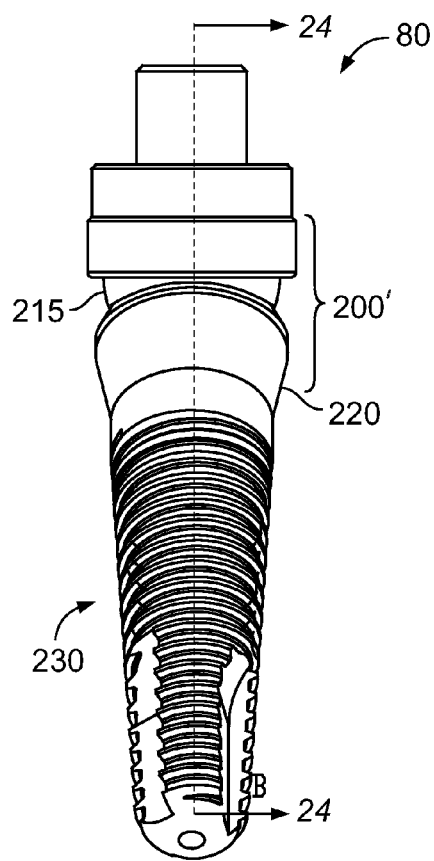
FIG. 23 is a side view of the assembled dental attachment device with a 20° pre-angled abutment of FIG. 21
Figure 24:
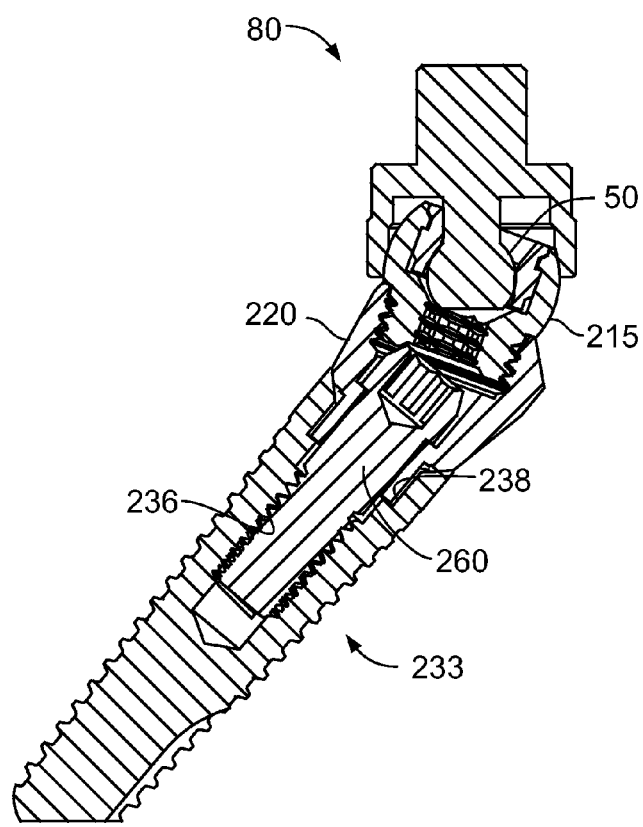
FIG. 24 is a cross-sectional view of FIG. 23.

The two-piece pre-angled abutment 200', as shown in FIGS. 23 and 24, can be assembled and secured in an implant 233 using a retaining screw 260 as shown in FIG. 24. The second attachment portion 225 of the second component 220 is fitted into cavity 238 of the implant 233. The retaining screw 260 is set through the through bore 239 and screwed into the threaded bore 236, thereby securing the second component 220 to the implant 230. The threaded shaft 227 of the first component 215 is engaged and secured into the threaded portion 251 of the cavity 236 of the second component 220.

Another embodiment of the abutment is incorporated as a mini implant for osseo-integration into the jawbone of a subject. A mini implant is a small-diameter, one-piece root form implant that osseo-integrates into the jawbone and allows immediate loading of a dental appliance. The mini implant come in a number of different sizes. The shaft may range in diameter from about 1.8 mm to about 2.9 mm. Illustratively, the diameter of the shaft may be about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm and about 2.9 mm. Further, the length of the shaft ranges from about 10 mm to about 18 mm. In further embodiments, the length may be about 10 mm, about 11 mm, about 12 mm, about 13 mm, about 14 mm, about 15 mm, about 16 mm, about 17 mm, and about 18 mm.

Figure 25:
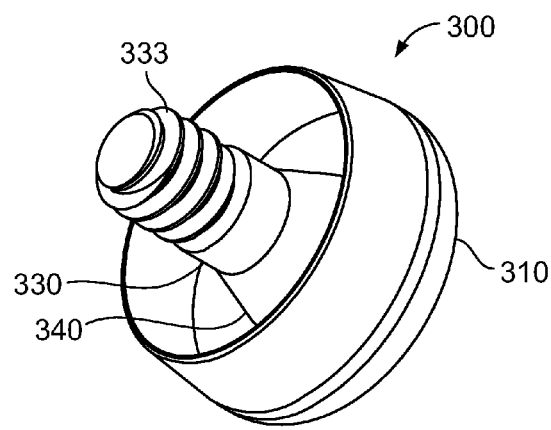
FIG. 25 is a perspective view of a healing cap.
Figure 26:
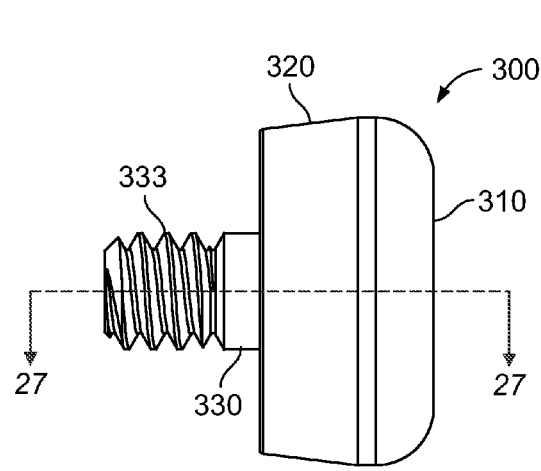
FIG. 26 is a side view of FIG. 25.
Figure 27:
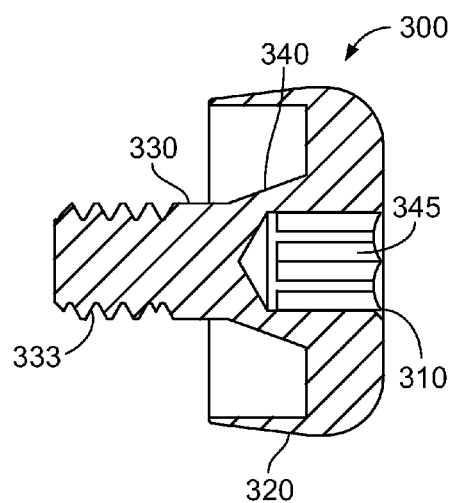
FIG. 27 is a cross-sectional view of FIG. 26.

FIGS. 25 to 27 illustrate one embodiment of a healing cap 300. The healing cap 300 comprises an upper surface 310 that is generally flat and an annular skirt 320 projecting downwardly from the upper surface 310 to surround a shaft 330. The shaft comprises a distal threaded portion 333 and a coaxial trunco-conical section 340. A tool-receiving bore 345 extends inwardly from the upper surface 310. The tool-receiving bore 345 can be, for example hexagonal with flat faces, for engagement by a suitable tool.

Figure 28:
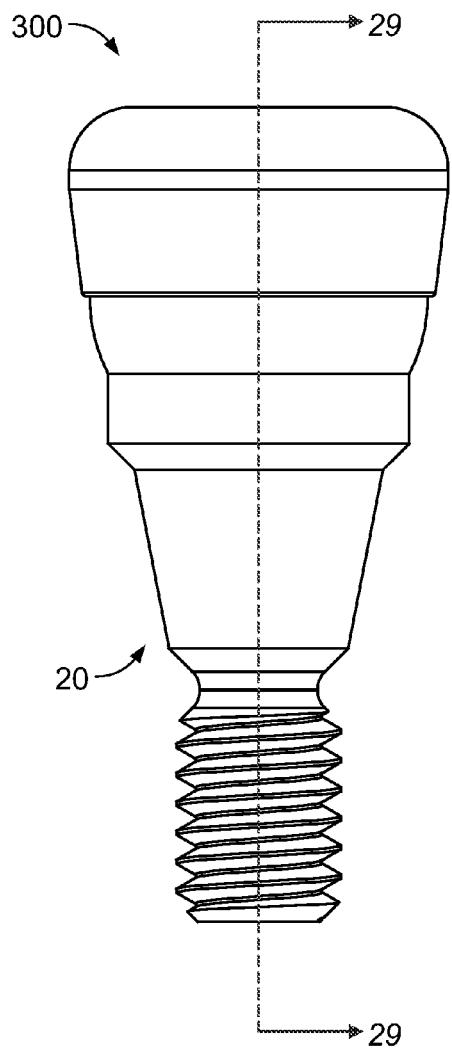
FIG. 28 is a side view of assembled healing cap on an abutment.
Figure 29:
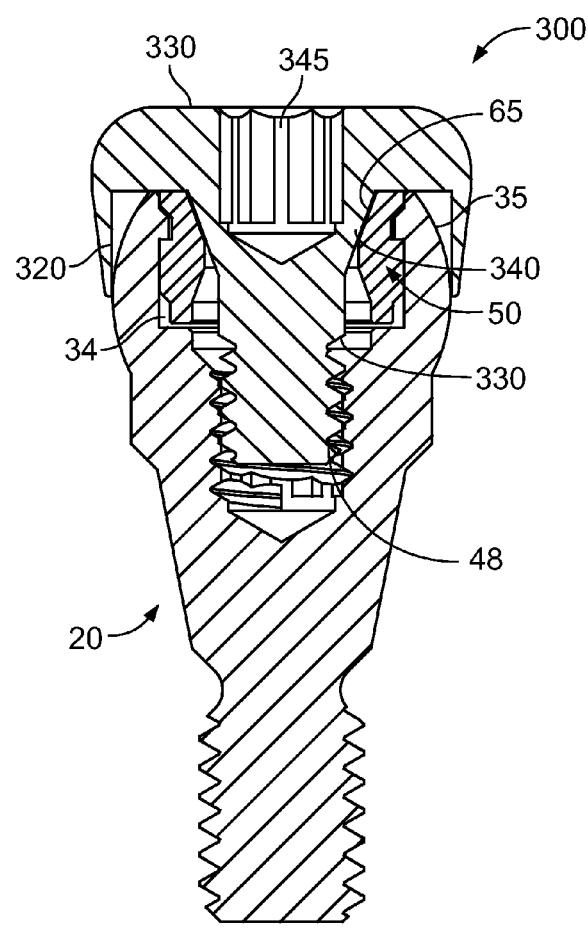
FIG. 29 is a cross-sectional view of FIG. 28.

Referring to FIGS. 28 and 29, the healing cap 300 is positioned over the socket 34 of the abutment 20 and the shaft is engaged through the ring 50 and screwed into the threaded bore 48. The tapered inner surface 65 of the ring 50 matches the trunco-conical section 340 of the shaft 330 of the healing cap 300. At the same time, the annular skirt 320 is engaged and tightened over the outer surface 35 of the abutment 80. The fit between the healing cap 300 and abutment 20 can help to create a seal that minimizes the penetration of oral fluids into the abutment cavity in an effort to prevent microbial contamination.

Figure 30:
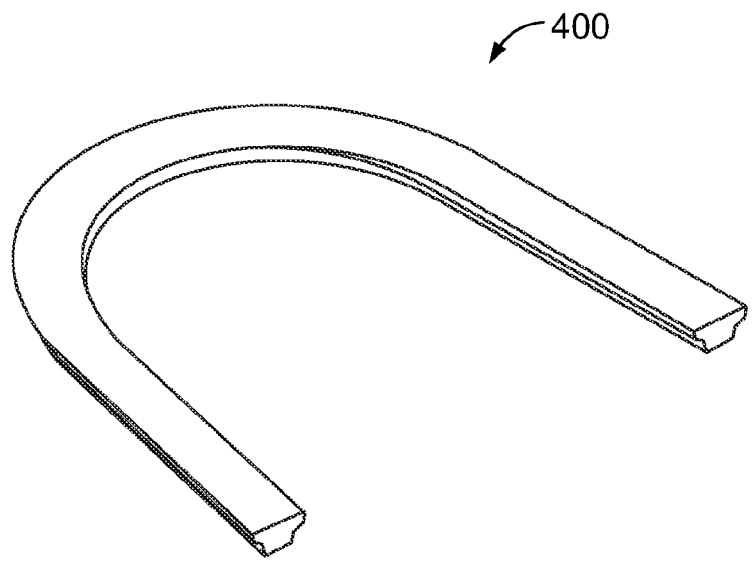
FIG. 30 is a perspective view of curved bar.
Figure 31:
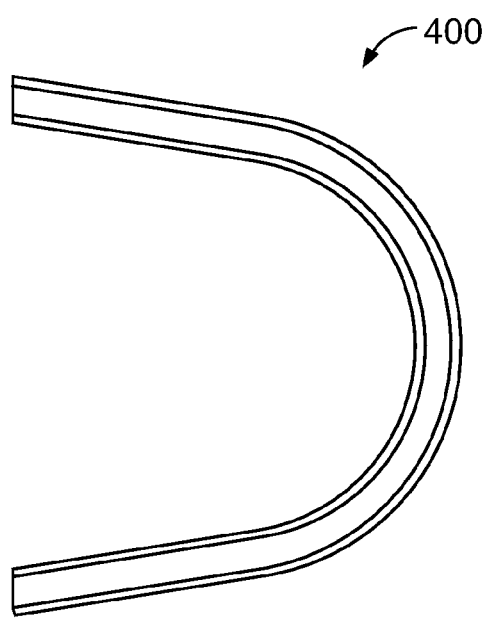
FIG. 31 is a top view of FIG. 30.

FIGS. 30 and 31 illustrates one embodiment of a curved bar attachment 400. The bar attachment 400 can be used to connect two or more dental attachment devices 10 to a rigid frame for a full denture, overdenture or partial denture. The bar 400 can be made in a number of different sizes to accommodate varying patients' dental arch, for example, small, medium, large, and extra large, and made of suitably strong material such as titanium, titanium alloys, cobalt-chromium-molybdenum alloys, stainless steel with a titanium nitride coating, zirconium, tantalum, gold, platinum, palladium, hafnium and tungsten, as well as other materials known to those of skill in the art. The bar may also be cut into partial arch shapes that are both straight and curved of various lengths.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein are representative of the subject matter which is broadly contemplated by the present invention. It is further understood that the scope of the present invention is not intended to be limited to the embodiment shown herein but is to be accorded the widest scope consistent with the patent law and the principles and novel features disclosed herein.

All references, including publications, patent applications, and patents, cited herein are hereby incorporated by reference to the same extent as if each reference were individually and specifically indicated to be incorporated by reference and were set forth in its entirety herein.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

The invention claimed is:

1. A fixed detachable dental attachment device, comprising:
   a cap having a first attachment portion adapted to be rigidly secured to a dental appliance and a body portion having an open end, a retention head and an inner cavity facing away from the dental appliance and forming an annular wall that surrounds the retention head, the annular wall having a concave portion extending up to the open end, wherein the first attachment portion and body portion are aligned along a central longitudinal axis of the cap;
   a ring; and
   an abutment comprising an upper portion and a second attachment portion, the upper portion having a convex outer surface comprising an open end and a socket for receiving the ring and the retention head, wherein an external surface of the ring contacts the socket and an internal surface of the ring contacts the retention head to secure the cap onto the abutment without contact between the retention head and the socket;
   wherein the concave portion of the annular wall of the body portion of the cap engages over the convex outer surface of the abutment to secure the cap onto the abutment; and
   the retention head is in swivel engagement in the ring and the concave portion of the inner cavity of the body portion of the cap is in direct swivel engagement with the convex outer surface of the abutment.

2. The device of claim 1, wherein the retention head comprises a head portion and a shaft.

3. The device of claim 2, wherein the head portion is ball-shaped.

4. The device of claim 2, wherein the head portion is in a shape selected from the group consisting of: spherical, polyhedron, and spheroid.

5. The device of claim 1, wherein the annular wall has a lower lip and the retention head projects beyond the lip of the annular wall and out of the inner cavity.

6. The device of claim 1, wherein the first attachment portion comprises a post.

7. The device of claim 1, wherein the abutment further comprises a cuff portion between the upper portion and second attachment portion.

8. The device of claim 1, wherein the second attachment portion is adapted to be compatible with commercially available implants.

9. The device of claim 1, wherein the second attachment portion is configured as a non-vital tooth root abutment, a mini-implant, or an intermediary abutment.

10. The device of claim 1, wherein the inner cavity of the body portion of the cap has an inner end facing the open end, and the abutment has an upper end facing away from the socket which is axially spaced from the inner end of the cavity to provide a first gap between the upper end of the abutment and the opposing inner end of the inner cavity in the cap, and the retention head has an end face spaced from the socket to provide a second gap between the retention head and socket, wherein the first and second gaps permit swivel engagement of the cap on the abutment over a range of divergence.

11. The device of claim 10, wherein the range of divergence between the cap relative to the abutment is at an angle from 0° to about 20°.

12. The device of claim 10, wherein cap diverges relative to the abutment at an angle selected from the group consisting of: 0°, about 1°, about 2°, about 3°, about 4°, about 5°, about 6°, about 7°, about 8°, about 9°, about 10°, about 11°, about 12°, about 13°, about 14°, about 15°, about 16°, about 17°, about 18°, about 19°, and about 20°.

13. A method of securing a dental appliance in a subject's mouth using the device of claim 1 comprising the steps of:
    a. attaching the abutment into an existing non-vital tooth root, implant, or intermediary abutment by means of the attachment portion;
    b. aligning the cap integral in the dental appliance over the abutment, and
    c. engaging the retention head through the ring and into the socket of the abutment thereby securing the cap onto the abutment.

14. The device of claim 1, wherein gaps between an upper axial end of the abutment and an opposing inner axial end of the inner cavity of the cap body portion and between the retention head and socket permit swivel movement of the cap on the abutment through a predetermined range of divergence while the concave portion maintains sealing engagement with the convex outer surface of the abutment.

15. The device of claim 1, wherein the retention head is rigidly secured in the cap.

16. A method of securing a dental appliance in a subject's mouth comprising the steps of:
    providing an abutment comprising an upper portion and an attachment portion, wherein the upper portion, having a convex outer surface, comprises an open end and a socket;
    inserting a ring into the socket;
    attaching the abutment into an existing non-vital tooth root, implant, or intermediary abutment through the attachment portion;
    aligning a cap over the abutment, wherein the cap has an attachment portion rigidly secured to or integral with a dental appliance and body portion next to and extending from the attachment portion, the body portion having an open end, a retention head and an inner cavity facing away from the dental appliance and forming an annular wall that surrounds the retention head;
    engaging the retention head through the ring and into the socket of the abutment and engaging a concave lower lip of the annular wall of the body portion over the convex outer surface of the abutment thereby securing the cap onto the abutment, wherein an external surface of the ring contacts the socket and an internal surface of the ring contacts the retention head, whereby the retention head is in swivel engagement in the ring, the concave lower lip of the annular wall is in direct swivel engagement with the convex outer surface of the abutment, and the dental appliance is secured to the abutment solely by the body portion of the cap.

17. The method of claim 16, wherein changes in the frictional force between the concave lip of the annular wall of the body portion of the cap and the outer convex surface of the abutment, or the angle of convergence thereof, vary the retentive force between the cap and abutment.

18. The method of claim 16, wherein a first gap between an upper axial end of the abutment and an opposing inner axial end of the inner cavity in the body portion of the cap and a second gap between the retention head and socket allow swiveling motion of the cap on the abutment through a predetermined angular range when the retention head is engaged through the ring and the cap is secured onto the abutment, and the concave lip of the body portion of the cap maintains sealing contact with the outer convex surface of the abutment during swiveling motion of the cap through the predetermined angular range.

19. A fixed detachable dental attachment device, comprising:
    a cap having a first attachment portion adapted to be rigidly secured to a dental appliance and a body portion next to the first attachment portion, the body portion having an open end, a retention head and an inner cavity facing away from the attachment portion and forming an annular wall that surrounds the retention head, the annular wall having a concave lip, wherein the first attachment portion and body portion are aligned along the central longitudinal axis of the cap;
    an abutment comprising an upper portion with a convex outer surface, the upper portion having an open end and a socket for receiving the retention head; and
    a ring snap fit into the socket and positioned between the socket and the retention head, the ring having an upper portion and a lower portion, wherein the retention head has a stem and an enlarged head portion of at least partially spherical shape which is snap fit into the lower portion of the ring and in swivel engagement with an opposing surface of the lower portion of the ring, and the concave lip of the annular wall of the body portion of the cap is in direct swivel engagement over the convex outer surface of the abutment to secure the cap onto the abutment, whereby the dental appliance is secured to the abutment solely by the body portion of the cap.

20. The fixed detachable dental attachment device of claim 19, wherein the inner surface of the ring is of hour-glass shape.

21. The fixed detachable dental attachment device of claim 19, wherein the ring is made of a durable and flexible material.

* * * * *